(12) United States Patent
Nguyen-Tuong et al.

(10) Patent No.: US 11,093,863 B2
(45) Date of Patent: Aug. 17, 2021

(54) METHOD FOR ASCERTAINING A TIME CHARACTERISTIC OF A MEASURED VARIABLE, PREDICTION SYSTEM, ACTUATOR CONTROL SYSTEM, METHOD FOR TRAINING THE ACTUATOR CONTROL SYSTEM, TRAINING SYSTEM, COMPUTER PROGRAM, AND MACHINE-READABLE STORAGE MEDIUM

(71) Applicants: ROBERT BOSCH GMBH, Stuttgart (DE); MAX-PLANCK-GESELLSCHAFT ZUR FÖRDERUNG DER WISSENSCHAFT E.V., Müchen (DE)

(72) Inventors: The Duy Nguyen-Tuong, Leonberg (DE); Christian Daniel, Leonberg (DE); Sebastian Trimpe, Tübingen (DE); Martin Schiegg, Korntal-Meunchingen (DE); Andreas Doerr, Stuttgart (DE)

(73) Assignees: MAX-PLANCK-GESELLSCHAFT ZUR FÖRDERUNG DER WISSENSCHAFT E.V.; ROBERT BOSCH GMBH

(*) Notice: Subject to any disclaimer, the term of this patent is extended or adjusted under 35 U.S.C. 154(b) by 0 days.

(21) Appl. No.: 16/965,897

(22) PCT Filed: Jan. 28, 2019

(86) PCT No.: PCT/EP2019/052026
§ 371 (c)(1),
(2) Date: Jul. 29, 2020

(87) PCT Pub. No.: WO2019/149664
PCT Pub. Date: Aug. 8, 2019

(65) Prior Publication Data
US 2021/0011447 A1    Jan. 14, 2021

(30) Foreign Application Priority Data
Jan. 30, 2018 (DE) .................... 10 2018 201 411.6

(51) Int. Cl.
*G05B 13/02* (2006.01)
*G06N 20/00* (2019.01)
(Continued)

(52) U.S. Cl.
CPC ............ *G06N 20/00* (2019.01); *G05B 19/042* (2013.01); *G06N 5/04* (2013.01); *A61B 6/03* (2013.01);
(Continued)

(58) Field of Classification Search
CPC ........ G05B 17/02; G05B 13/027; G05B 5/01; G05B 19/042; G05B 2219/25316;
(Continued)

(56) References Cited

U.S. PATENT DOCUMENTS 5,010,473 A * 4/1991 Jacobs .................. A61M 5/172
604/65
2003/0028266 A1 * 2/2003 Jacques .................... G05B 5/01
700/32
(Continued)

FOREIGN PATENT DOCUMENTS

DE        202017102235 U1    5/2017

OTHER PUBLICATIONS

Stefanos Eleftheriadis et al., "Identification of Gaussian Process State Space Models," 31st Conference on Neural Information Processing Systems (NIPS 2017), Long Beach, CA, USA. ARXIV preprint arxiv:1705.10888V2, 2017, 11 pages.
(Continued)

*Primary Examiner* — Tuan A Vu
(74) *Attorney, Agent, or Firm* — Robert Plotkin; Blueshift IP

(57) ABSTRACT

A method for ascertaining a time characteristic of a measured variable adjustable by an actuator, wherein a time characteristic of a control variable is applied to the actuator, wherein the ascertaining is effected by means of a Gaussian process state model of the behavior of the actuator, wherein the time characteristic of the measured variable of the actuator is ascertained on the basis of a parameterizable family of functions, wherein in the parameterizable family of functions a time dependency of a later latent state, in
(Continued)

particular ascertained using a transfer function, of the actuator on an earlier latent state of the actuator and an earlier control variable of the actuator is the same as the applicable dependency of the Gaussian process state model.

11 Claims, 5 Drawing Sheets

(51) Int. Cl.
  *G05B 19/042* (2006.01)
  *G06N 5/04* (2006.01)
  *F02D 41/28* (2006.01)
  *G05B 5/01* (2006.01)
  *A61B 6/03* (2006.01)
  *H01L 41/04* (2006.01)

(52) U.S. Cl.
  CPC ............... *F02D 41/28* (2013.01); *G05B 5/01* (2013.01); *G05B 13/027* (2013.01); *G05B 2219/25316* (2013.01); *H01L 41/042* (2013.01)

(58) Field of Classification Search
  CPC ......... A61B 6/03; H01J 37/263; A61M 5/172; F02D 41/28; H01L 41/04; G06N 5/04; G06N 20/00
  See application file for complete search history.

(56) References Cited

U.S. PATENT DOCUMENTS

| | | | | |
|---|---|---|---|---|
| 2004/0173748 | A1* | 9/2004 | Dirksen | H01J 37/263 250/310 |
| 2011/0282517 | A1* | 11/2011 | Streichert | F02D 41/28 701/1 |
| 2012/0053704 | A1* | 3/2012 | MacArthur | G05B 17/02 700/29 |
| 2016/0071006 | A1* | 3/2016 | Grothmann | G05B 13/027 706/16 |
| 2016/0324403 | A1* | 11/2016 | Yeoh | H01L 41/042 |
| 2018/0106734 | A1* | 4/2018 | Lang | A61B 6/03 |

OTHER PUBLICATIONS

International Search Report and Written Opinion dated May 28, 2019, in international patent application No. PCT/EP2019/052026, 9 pages.

César Lincoln et al., "Recurrent Gaussian processes," arXiv preprint arXiv:1511.06644.v6, 2016, 12 pages.

Andreas Svensson et al., "A flexible state space model for learning non-linear dynamical systems," arXiv preprint arXiv:1603.05486v2, 2017, 19 pages.

Roger Frigola et al., "Variational Gaussian Process State-Space Models," arXiv preprint arXiv:1406.4905v2, 2014, 12 pages.

\* cited by examiner

METHOD FOR ASCERTAINING A TIME CHARACTERISTIC OF A MEASURED VARIABLE, PREDICTION SYSTEM, ACTUATOR CONTROL SYSTEM, METHOD FOR TRAINING THE ACTUATOR CONTROL SYSTEM, TRAINING SYSTEM, COMPUTER PROGRAM, AND MACHINE-READABLE STORAGE MEDIUM

PRIOR ART

From "Variational Gaussian Process State-Space Models," arXiv preprint arXiv:1406.4905v2, 2014, Roger Frigola, Yutian Chan and Carl E. Rasmussen, a method for variational Bayesian learning of a non-linear state-space model is known by means of sparse Gaussian processes.

From "Identification of Gaussian Process State Space Models," arXiv preprint arXiv:1705.10888v2, 2017, Stefanos Eleftheriadis, Thomas F. W. Nicholson, Marc Peter Deisenroth and James Hensman as well as "A flexible state space model for learning non-linear dynamical systems," arXiv preprint arXiv:1603.05486v2, 2017, Andreas Svensson and Thomas B. Schön, further methods for learning state space models are known.

ADVANTAGE OF THE INVENTION

In contrast, the method having the features of independent claim 1 has the advantage that a particularly efficient and robust method is to learn nonlinear state space models even in the case of high-dimensional latent state spaces.

Advantageous further developments are the subject matter of the independent claims.

DISCLOSURE OF THE INVENTION

In a first aspect, the invention relates to a method for ascertaining a time characteristic of a measured variable y, which is adjustable by an actuator, a time characteristic of a control variable u being applied to the actuator.

The ascertaining is carried out by means of a Gaussian process state space model (abbreviated GP-SSM), which describes the behavior of the actuator. Here, a control variable of the actuator is ascertained on the basis of a parameterizable family of functions $q(x_{1:T}, f_{2:T}, z)$.

State space models, also called state models, describe the behavior of a system by means of a latent variable x under a transfer model f and process noise $\epsilon_x$. On the basis of the latent variable x, a measured variable y is ascertained by means of an observation function g with measurement noise $\epsilon_y$. As usual, a time trend can be described by means of a subscript "t." A state space model is then given as $$x_{t+1} = f(x_t, u_t) + \epsilon_x$$
$$y_t = g(x_t) + \epsilon_y \qquad (1)$$

With Gaussian processes, distributions can be represented by functions. This allows a priori assumptions about the behavior of a system to be taken into account. In this case, for a set of observations $X=[x_1, \ldots, x_N]$, the corresponding function values $f=[f(x_1), \ldots, f(x_N)]$ are assumed to be Gaussian distributed, i.e.

$$p(f|X) = \mathcal{N}(f|m_X, K_{X,X}), \qquad (2)$$

with mean vector $m_X$ with entries $m_i = m(x_i)$ and a covariance matrix $K_{X,X}$ with elements $K_{ij} = k(x_i, x_j)$. As usual, $\mathcal{N}$ designates a normal distribution. The entries of the mean vector $m_X$ can be chosen to be zero, for example The function $k(x_i, x_j)$ can be given with suitable hyperparameters $\sigma_f^2$, $\Lambda = \text{diag}(l_1^2 \ldots l_N^2)$, for example by $$k(x_i, x_j) = \sigma_f^2 \exp\left(-\frac{1}{2}(x_i - x_j)^T \Lambda^{-1}(x_i - x_j)\right).$$

For given function values f on observations X, the conditional probability distribution can be written at a new observation point x* as $$p(f^*|x^*, f, X) = \mathcal{N}(f^*|\mu, \sigma^2) \qquad (3)$$

with $\mu = m_x^* + k_x^*{}_{,X} K_{X,X}^{-1}(f - m_X)$, $\sigma^2 = k_{x^*,x^*} - k_x^*{}_{,X} K_{X,X}^{-1} k_{X,x^*}$, wherein $k_{A,B}$ designates a scalar or vector of covariances for each pair of elements in A, B. It is important here that the kernel is selected so that the functions $\mu, \sigma$ can be differentiated by x*.

With the abbreviation $\hat{x}_t = (x_t, u_t)$, the transfer model can also be written as $f_{t+1} = f(\hat{x}_t)$. A time series of observed measured variables y from a point in time a to a later point in time b is abbreviated as $y_{a:b}$ (analogously for other variables).

The descriptive Gaussian process can advantageously be implemented as a sparse Gaussian process. For this purpose, inducing Gaussian process targets $z=[z_1, \ldots, z_P]$ at predeterminable pseudo input points $\zeta=[\zeta_1, \ldots, \zeta_P]$ can be provided. This reduces the computational effort for adapting the parameters of the Gaussian process, especially with large training data records.

A Gaussian process can be chosen for the transfer model f as well as for the observation function g. For the identification of the parameters characterizing the Gaussian process, however, it is helpful to choose a known parametric observation model, for example $$p(y_t|x_t) = \mathcal{N}(y_t|g(x_t), R) \qquad (4)$$

with diagonal covariance matrix $R = \text{diag}(\sigma_{y,1}^2, \ldots, \sigma_{y,D_y}^2)$ and observation function $$g(x_t) = C x_t, \qquad (5)$$

wherein the matrix C is selected such that it selects the $D_y$ first entries of the latent variable $x_t$, i.e. $C=[I,0] \in \mathbb{R}^{D_y, D_x}$, wherein I is the unit matrix. In this case, the dimension of the space of the latent variable x is designated with $D_x$, the dimension of the space of the measured variable y is designated with $D_y$. This model is particularly suitable for $D_y < D_x$, which is usually the case in systems with a limited number of physical sensors, such as robots. The observation function g can also be provided by another parametric, differentiable mapping. For high-dimensional observation spaces, i.e. large $D_y$, another differentiable function, for example a neural network, can also be used as the observation function g, for example.

The common distribution function of the variables of the GP-SSM can then be written as $$p(y_{1:T}, x_{1:T}, f_{2:T}, z) = \prod_{t=1}^{T} p(y_t|x_t) \times \prod_{t=2}^{T} p(x_t|f_t) p(f_t|\hat{x}_{t-1}, z) \times p(x_1) p(z). \qquad (6)$$

In this case, $p(f_t|\hat{x}_{t-1}, z) = \prod_{d=1}^{D_x} p(f_{t,d}|\hat{x}_{t-1}, z_d)$ and $z = [z_1, \ldots, z_{D_x}]$.

The process noise can be chosen as $p(x_t|f_t)=\mathcal{N}(x_t|f_t,Q)$ with diagonal covariance $Q=\text{diag}(\sigma_{x,1}^2, \ldots, \sigma_{x,D_x}^2)$. The initial distribution of the latent states $p(x_1)$ is unknown. The transfer dynamics for each latent dimension d are described independently by $p(f_{t,d}|\hat{x}_{t-1},z_d)p(z_d)$. This probability can be selected by the sparse Gaussian a-posteriori probability distribution $$p(f_{t,d}|\hat{x}_t,z_d,\zeta_d) \approx p(f_{t,d}|\hat{x}_t,f,X) \tag{7}$$

analogous to equation (3). The a-priori probability distribution $p(z_d)$ of the inducing targets $z_d$ can also be selected with normal distribution using suitable parameters $m_\zeta$, $K_{\zeta,\zeta}$:

$$p(z_d)=\mathcal{N}(m_{\zeta_d},K_{\zeta_d,\zeta_d}) \tag{8}$$

The integration that is necessary to ascertain a log-likelihood or an a-posteriori probability distribution for the model given by equation (6) is very difficult to solve. Therefore, there are approaches to use a variation function.

From "Recurrent Gaussian processes," arXiv preprint arXiv:1511.06644.v6, 2016, César Lincoln C. Mattos, Zhenwen Dai, Andreas Damianou, Jeremy Forth, Guilherme A. Barreto, Neil D. Lawrence, for example, it is known to introduce a so-called mean field approximation for the latent states $x_{1:T}$. Here, the a-posteriori probability distribution $p(x_{1:T}, f_{2:T}, z|y_{1:T})$ of a model given by equation (6) is approximated by a family of factorized approximation functions q of the form $$q(x_{1:T}, f_{1:T}, z) = \Pi_{t=1}^T q(x_t) \Pi_{d=1}^{D_x} q(z_d) \Pi_{t=1}^T p(f_t|z,x_t). \tag{9}$$

By varying the parameters that parameterize this family, an attempt can then be made to best approximate the actual a-posteriori probability distribution.

In order to better maintain the time correlations between states in the model (6), the parameterizable family of functions $q(x_{1:T},f_{2:T},z)$ can be selected instead of the above-mentioned approach such that a time dependency of the later latent states x of the actuator is retained. In other words, the dependency of a later latent state $x_t$ of the actuator (which was ascertained, for example, with a transfer function) on an earlier latent state x of the actuator, in particular immediately earlier, and an earlier control variable u of the actuator, in particular immediately earlier, should be equal to that applicable dependency of the Gaussian process state model, in particular according to equation (6). This means that the dependency formulated by the term $p(f_t|\hat{x}_{t-1})$ or (in the case of sparse wording) $p(f_t|\hat{x}_{t-1},z)$ in equation (6) should also be preserved in the parameterizable family of functions $q(x_{i:T}, f_{2:T},z)$.

In particular, it can be provided that the parameterizable family of functions $q(x_{1:T},f_{2:T},z)$ is configured to approximate an a-posteriori probability distribution $p(x_{1:T},f_{2:T}, z|y_{1:T})$ as well as possible for an ascertained training data record $y_{mess}$.

The training data record $y_{mess}$ is advantageously ascertained by controlling the actuator with a predeterminable training characteristic $u_{1:n}$ of the predeterminable control variable u and ascertaining a resulting time training characteristic $y_{1:n}$ of the measured variable y. The training data record $y_{mess}$ can then be given by $(y_{1:n},u_{1:n})$.

The dependency of the parameterizable family of functions $q(x_{1:T},f_{2:T},z)$ on an initial latent state $x_1$ of the actuator is advantageously given by a factor that depends on this initial latent state $x_1$ (in particular only depends thereon), this factor being given by a parameterizable variation function $q(x_1)$, in particular by a normal distribution $\mathcal{N}(m_{x1}, S_{x1})$.

Alternatively or additionally, a dependency of the parameterizable family of functions $q(x_{1:T},f_{2:T},z)$ on Gaussian process targets $z_d$ is given by a second factor, this second factor having a second parameterizable variation function $q(z_d)$, which has the respective Gaussian process target $z_d$ as an argument.

The second parameterizable variation function $q(z_d)$ can be given by a normal distribution function $\mathcal{N}(z_d|m_d,S_d)$.

The parameterizable family of functions then takes the form $$q(x_{1:T}, f_{1:T}, z) = \prod_{t=2}^T p(x_t|f_t) \times \prod_{t=2}^T \prod_{d=1}^{D_x} P(f_{t,d}|\hat{x}_{t-1},z_d)q(z_d) \times q(x_1). \tag{10}$$

The parameters with which this parameterizable family of functions is parameterized are then given by
Process noise
Sensor noise
Variation parameters for the inducing Gaussian process targets
Predeterminable pseudo input points
Kernel hyperparameters.

With this parameterizable family of functions, it can now be provided that a predicted time trend of the latent state $\tilde{x}_t$ of the actuator is ascertained by recursively ascertaining a sample of the predicted time trend of the latent state at a later point in time $\tilde{x}_{t+1}$ from the parameterizable variation function of the predicted latent state at the later point in time given the predicted latent state at a previous point in time $q(\tilde{x}_{t+1}|\tilde{x}_t)$, the control variable of the actuator being chosen on the basis of the predicted time trend of the latent state.

As shown in more detail in the exemplary embodiments, this allows a simple ascertainment of a lower variational barrier, which is also known as ELBO.

Due to the Markov structure of the latent states x and the sparse Gaussian process approximation, the (marginalized) approximated distribution of the latent state at a time t, $q(x_t)$ is conditionally independent of earlier time steps in the case of a given distribution at an earlier point in time t−1. This allows the recursive procedure described above.

However, it is necessary to specify an initial latent state $\tilde{x}_1$. It is either possible for the initial latent state $\tilde{x}_1$ of the predicted time trend of the latent state to be fixed, in particular to be specified randomly. This is particularly easy.

However, it is also possible that the initial latent state $(\tilde{x}_1)$ is ascertained from the parameterizable variation function $q(x_1)$ by a distribution function of the initial state $x_1$ given the ascertained training data record $q(x_1|y_{1:n},u_{1:n})$, the characterizing parameters of which are trained by back propagation.

In a further aspect, the invention relates to a method in which an optimal control variable $u_{opt}$, with which the actuator can be controlled, is ascertained on the basis of a characteristic of the measured variable y ascertained by means of one of the aforementioned methods. This allows optimal control of the actuator in a particularly simple manner In a further aspect, the invention relates to a method for learning a control strategy, which is also known under the term "policy learning." It can be provided that at least one optimal parameter $\xi_{opt}$ is ascertained. This optimal parameter $\xi_{opt}$ characterizes a control strategy of an actuator control system. This is set up on the basis of this control strategy to control the actuator with a control variable u. The control variable u can thus be ascertained on the basis of the control strategy and thus on the basis of the optimal parameter $\xi_{opt}$. A time characteristic of the measured variable y resulting from the application of the control strategy is determined by means of one of the aforementioned methods, and the at least one optimal parameter $\xi_{opt}$ is determined on the basis of the thus ascertained characteristic of the measured variable y.

In a further aspect, the invention relates to a method for training an actuator control system which is set up to carry out one of the aforementioned methods, wherein parameters which characterize the parameterizable family of functions $q(x_{1:T}, f_{2:T}, z)$ and/or deterministic model parameters are adapted such that they approximates the a-posteriori probability distribution $p(x_{1:T}, f_{2:T}, z | y_{1:T})$ of at least time characteristics of at least the latent state of the actuator $x_{1:T}$ and the transfer function $f_{2:T}$, given the time characteristic of the measured variable $y_{1:T}$ of the actuator as closely as possible for an ascertained training data record.

Hereinafter, embodiments of the invention will be explained in more detail with reference to the accompanying drawings. In the drawings.

DESCRIPTION OF THE EXEMPLARY EMBODIMENTS

Figure 1:
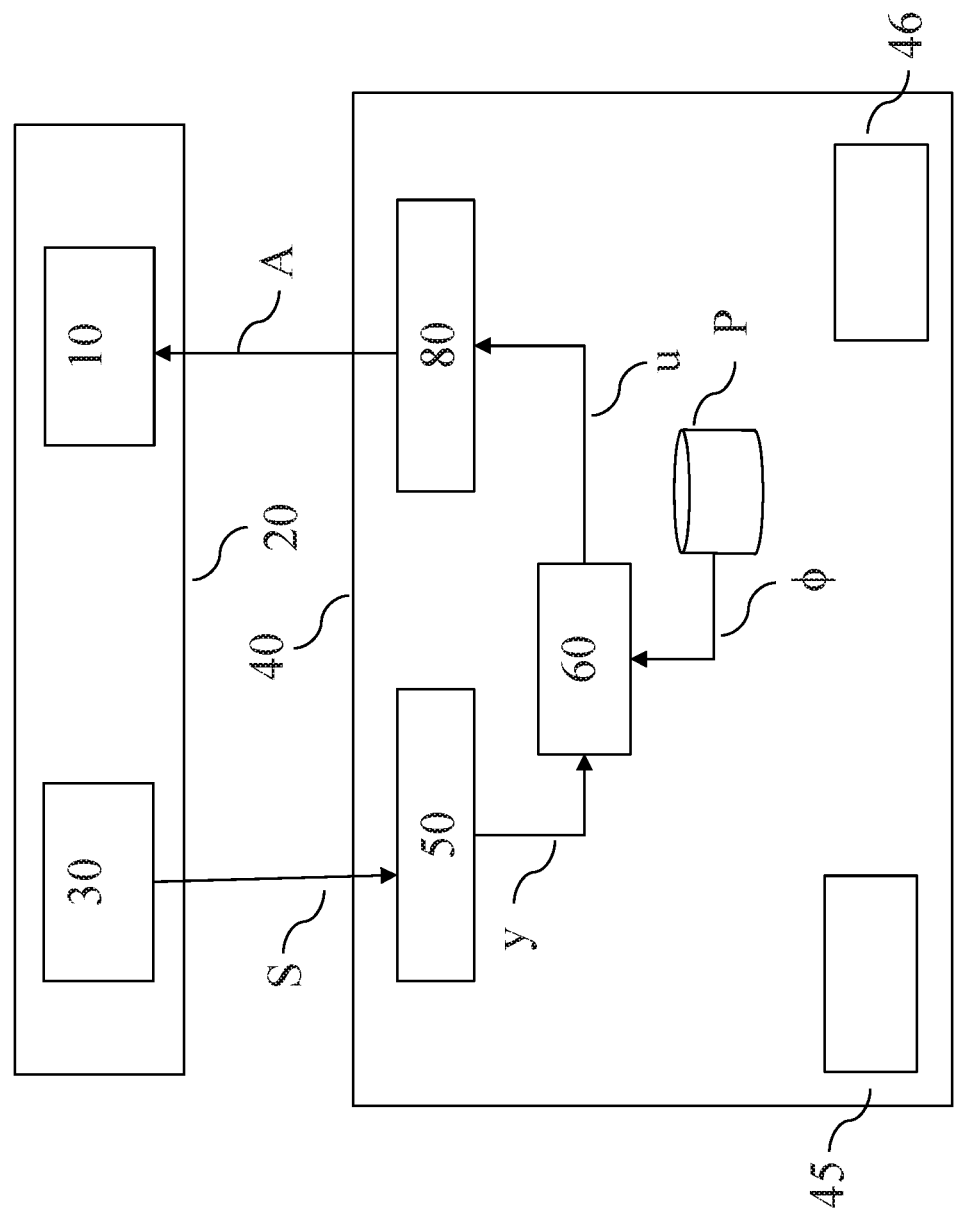
FIG. 1 shows schematically a structure of embodiments of the invention.

FIG. 1 illustrates a structure of possible embodiments of the invention. In one embodiment, FIG. 1 shows an actuator 10 in its environment 20 in interaction with an actuator control system 40. The actuator 10 and the environment 20 are collectively referred to below as the actuator system. At regular time intervals, for example a state of the actuator system is detected by a sensor 30, which may also be provided by a plurality of sensors. One sensor signal S each from the sensor 30 is transmitted to the actuator control system 40. The actuator control system 40 thus receives a sequence of sensor signals S. The actuator control system 40 uses this for ascertaining a sequence of control signals A which the actuator 10 receives.

The actuator 10 can be, for example, a (partially) autonomous robot, for example a (partially) autonomous motor vehicle, or a robot that combats targeted weeds in a field, for example tears them out or sprays them with applicable chemicals.

The sensor 30 may be, for example, one or a plurality of video sensors and/or one or a plurality of radar sensors and/or one or a plurality of ultrasonic sensors and/or one or a plurality of position sensors (for example GPS). Alternatively or additionally, the sensor 30 can also include an information system that ascertains information about a state of the actuator system, such as a weather information system that determines a current or future state of the weather in the environment 20.

In another exemplary embodiment, the actuator 10 may be a manufacturing robot, and the sensor 30 may then be, for example, an optical sensor that detects characteristics of manufacturing products of the manufacturing robot.

In a further exemplary embodiment, the actuator 10 can be a release system which is set up to enable or not to enable the activity of a device. The sensor 30 can be, for example, an optical sensor (for example for recording image or video data), which is set up to detect a face. Depending on the sequence of control signals A, the actuator 10 ascertains an enable signal that can be used to enable the device on the basis of the value of the enable signal. The device can, for example, be a physical or logical access control. Depending on the value of the control signal A, the access control can then provide that access is granted or not.

In a further exemplary embodiment, the actuator 10 can be part of a building control system, for example a controller of a heating system.

The actuator control system 40 receives the sequence of sensor signals S from the sensor in an optional receiving unit 50, which converts the sequence of sensor signals S into a sequence of measured variables y (alternatively, the sensor signal S can also be directly adopted as the measured variable y). The measured variable y can be, for example, a section or further processing of the sensor signal S. The measured variable y is fed to a machine learning system 60, the functioning of which is explained in more detail below in connection with FIG. 4.

The machine learning system 60 ascertains a control variable u from the measured variables y. This ascertainment is made on the basis of parameters φ, which are stored in a parameter memory P. These parameters φ can in particular include parameters $\xi_{opt}$ which characterize a control strategy of the actuator control system 40. The parameter memory P can be integrated in the actuator control system 40, but it can also be spatially separate from the actuator control system 40, and can be connected to the actuator control system 40, for example, via a network connection. The control variable u is fed to an optional forming unit 80, which ascertains therefrom control signals A which are fed to the actuator 10.

In further embodiments, the actuator control system 40 comprises the actuator 10.

In further preferred embodiments, the actuator control system 40 comprises a single or a plurality of processors 45 and at least one machine-readable storage medium 46 having stored thereon instructions which, when executed on the processors 45, cause the actuator control system 40 to execute the method for controlling the actuator 10.

Figure 2:
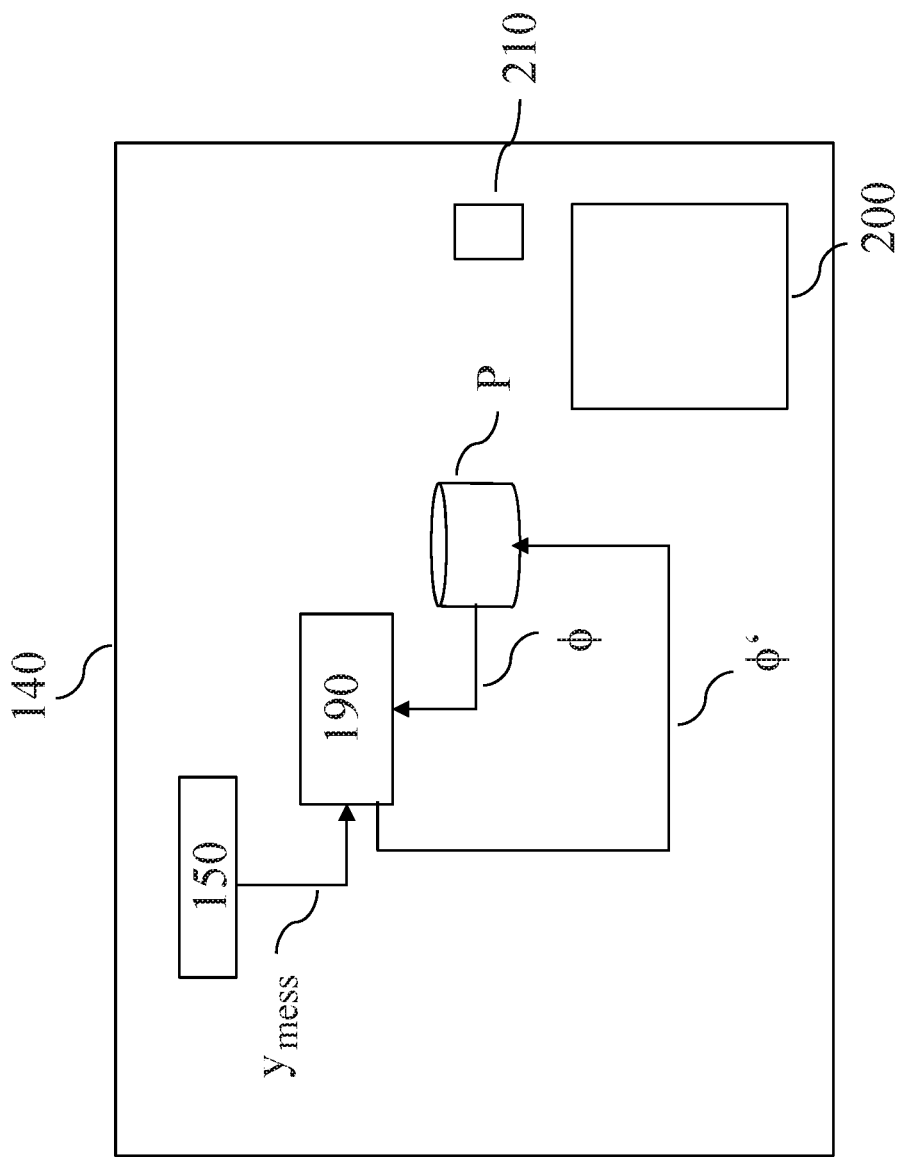
FIG. 2 shows schematically a structure of further embodiments of the invention.

FIG. 2 illustrates a machine training system 140 with which the machine learning system 60 of the actuator control system 40 can be trained.

A measurement apparatus 150 ascertains a training data record $y_{mess}$, which comprises both control variables u and associated measured variables y. These can be ascertained, for example, by actuating the actuator 10 by means of the control variables u and ascertainment of the resulting measured variables y, and can be stored on a data carrier (not shown), which can be part of the measurement apparatus 150. For the ascertainment of the training data record $y_{mess}$, the measurement apparatus 150 can read out from the data carrier.

Figure 3:
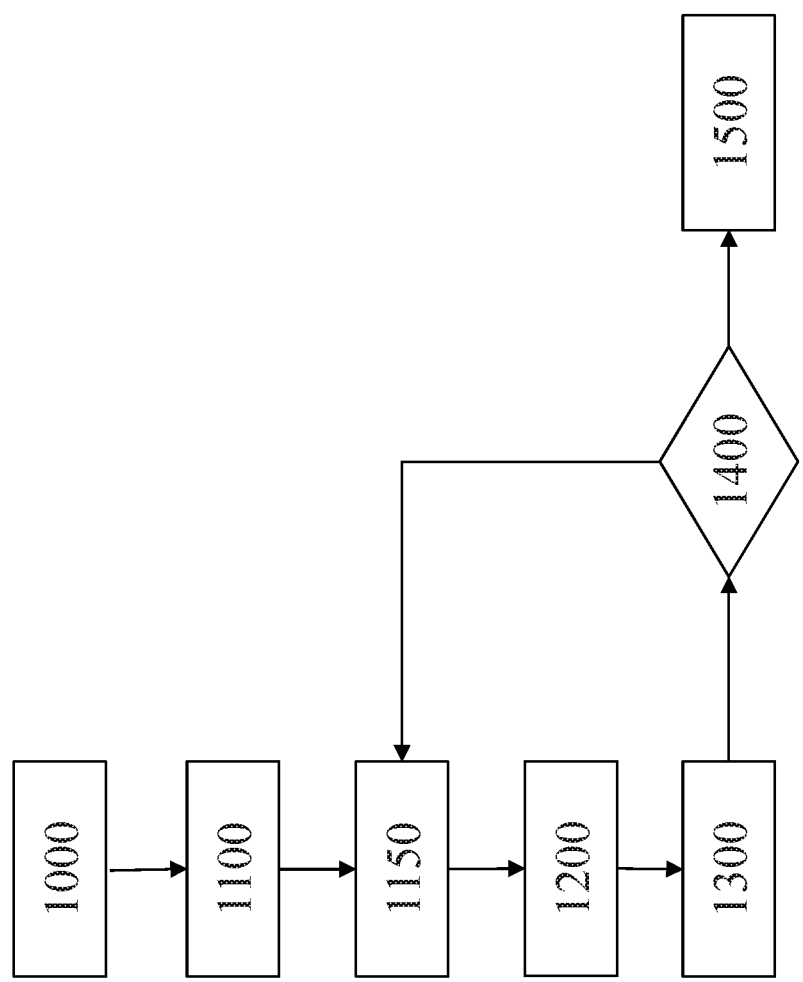
FIG. 3 is a flowchart of the sequence of a method according to one aspect of the invention.

The training data record $y_{mess}$ is fed to a training block 190 which, on the basis of the parameters φ stored in the parameter memory P, ascertains optimized parameters φ' by means of the method illustrated in FIG. 3, which replace the stored parameters φ in the parameter memory P.

Figure 5:
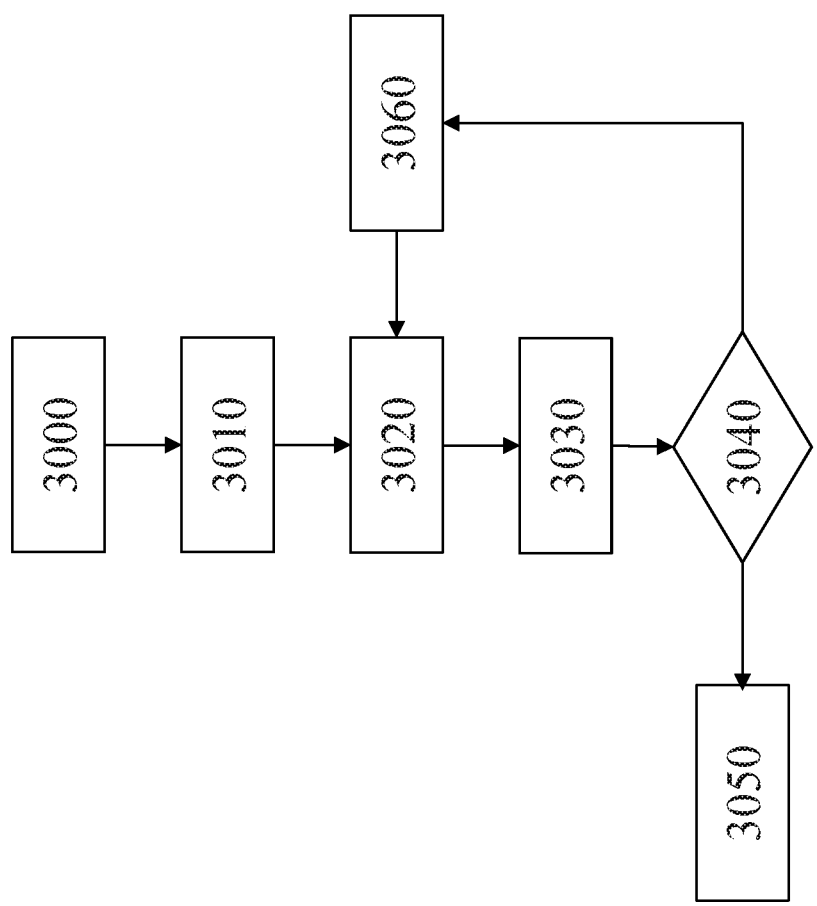
FIG. 5 is a flowchart of the sequence of a method according to yet another aspect of the invention.

Alternatively or additionally, by means of the method illustrated in FIG. 5, optimized parameters $\xi_{opt}$ can be ascertained, which can be part of the optimized parameters φ', and are also stored in the parameter memory P.

In other preferred embodiments, the training system 140 comprises one or a plurality of processors 200 and at least one machine-readable storage medium 210 having stored thereon instructions which, when executed on the processors 200, cause the training system 140 to carry out the method for training the machine learning system 60.

FIG. 3 illustrates an embodiment of a method for training the machine learning system 60. Initially (1000), the parameters φ are initialized and a training data record with time characteristics of the control variable u and the measured variable y is provided. The applicable time characteristics are designated with $u_{1:T}$ or $y_{1:T}$.

Subsequently (1100), these time characteristics are optionally divided into sub-characteristics of predeterminable length $T_{sub}$.

Thereafter, for the characteristic or one or more of the sub-characteristics, a plurality of sub-characteristics, in each case one or a plurality of associated trajectories of predicted latent variables x̃ is ascertained. For this purpose, an initial predicted latent state x̃₁ is first ascertained, for example, drawn from the parameterized distribution function $q(x_1)$. The parameters of this distribution function are then preferably also part of the parameters φ to be optimized, since any errors which are caused by the initial latent state may not decay sufficiently quickly, particularly in the case of short time characteristics. Thereafter, depending on the length of the time characteristic, a recursive ascertainment of the further predicted latent states x̃ₜ takes place.

Subsequently, samples x̃ₜ are taken from the distribution function $q(x_t)$. For this purpose, samples $\epsilon \sim \mathcal{N}(0,1)$ are taken, for example, and then are taken for all d and all points in time t>1

$$\tilde{x}_{t+1,d} = \mu_d + \epsilon \sqrt{\sigma_d^2(\tilde{x}_t, \tilde{x}_t) + \sigma_{x,d}^2}. \quad (11)$$

Herein $\tilde{x}_t = (\tilde{x}_t, u_t)$.

Thereafter, the parameters φ should be adjusted in such a way that the Kullback-Leibler divergence $KL(q(x_{1:T}, f_{2:T}, z) \| p(x_{1:T}, f_{2:T}, z | y_{1:T}))$ is minimized, the length T being naturally replaced by $T_{sub}$ in the case of subdivision into sub-characteristics. With the usual lower evidence lower bound (in short: ELBO), minimizing this KL divergence is equivalent to maximizing the ELBO that is given by $$\mathcal{L}_{GP-SSM} = \mathbb{E}_{q(x_{1:T}, f_{2:T}, z)} \left[ \frac{p(y_{1:T}, x_{1:T}, f_{2:T}, z)}{q(x_{1:T}, f_{2:T}, z)} \right] \quad (12)$$

$$= \sum_{t=1}^{T} \mathbb{E}_{q(x_t)}[\log p(y_t | x_t)] - \sum_{d=1}^{D} KL(q(z_d) \| p(z_d; \zeta_d)). \quad (13)$$

Therefore (1200), the ELBO is now estimated according to equation (13). For this purpose, the first term on the right-hand side from equation (13) is estimated using the predicted time characteristics of the latent variable x by means of $$\mathbb{E}_{q(x_t)}[\log p(y_t | x_t)] \approx \frac{1}{N} \sum_{i=1}^{N} \log p(y_t | x_t^i), \quad (14)$$

wherein N designates the predicted time characteristics of the latent variable x generated in step 1100.

On the basis of this stochastic ascertainment of the ELBO, gradients of the function $\mathcal{L}_{GP-SSM}$ are ascertained, and a stochastic gradient increase of the parameters φ is carried out in order to determine new parameters φ' (1300).

Now (1400), it is checked whether a convergence criterion is satisfied. If this is the case (1500), the new parameters φ' replace the parameters stored in the parameter memory P φ, and the method ends. Otherwise, the process branches back to step 1150.

Figure 4:
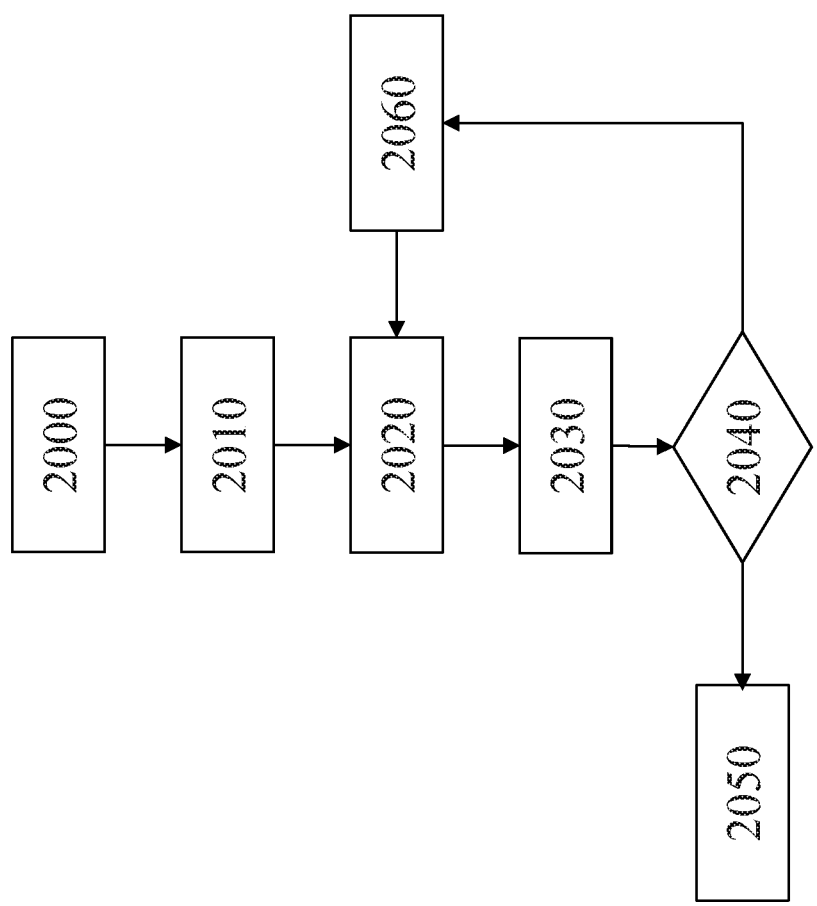
FIG. 4 is a flow-chart of the sequence of a method according to a further aspect of the invention.

FIG. 4 illustrates an embodiment of a method for controlling the actuator 10. Optionally, the training method illustrated in FIG. 3 is first carried out (2000). Thereafter (2010-2050), a model predictive adjustment is carried out on the control variable u for a predeterminable prediction horizon $T_{pred}$.

For this purpose, a time characteristic of the control variable u is first generated (2010). Subsequently, (2020) the initial latent state x̃₁ is ascertained, for example chosen randomly or chosen equal to 0. This is possible because, for stable transient dynamics, transient effects caused by an incorrectly selected initial latent state x̃₁ decay exponentially. The latent state $\tilde{x}_{1:T_{pred}}$ is subsequently determined, for example, using equation (11), and the measured variable $y_{1:T_{pred}}$ is also ascertained by means of the observation function g (given, for example, by equation (5)).

Thereafter (2030), a cost function is determined depending on the ascertained characteristic of the measured variable $y_{1:T_{pred}}$.

Subsequently (2040), it is checked whether a convergence criterion of the cost function has been reached. If this is the case (2050), the currently ascertained characteristic of the control variable u is adopted as the optimal control variable $u_{opt}$, and the actuator 10 is controlled according to the characteristic of the optimal control variable $u_{opt}$.

If this is not the case (2060), the characteristic of the control variable u is varied. For example, a gradient descent method can be used, the gradients being able to be ascertained numerically, for example, with evaluation steps analogous to step (2020), or being able to also be predetermined analytically. Subsequently, with a changed characteristic of the control variable u, the process branches back to step 2020.

FIG. 5 illustrates an embodiment of the method for ascertaining the parameter $\xi_{opt}$. Optionally, the training method illustrated in FIG. 3 is first carried out (3000).

Subsequently (3010), an initial value of the control variable u and an initial value of the parameter $\xi_{opt}$ are generated. An initial value of the latent state x is also ascertained analogously to step (2020). Subsequently (3020), by means of equations (5) and (11) and the current control strategy characterized by the parameter $\xi_{opt}$, a time characteristic of the latent state u, the measured variable y, and the control variable u is ascertained. Thereafter, a cost function is ascertained (4030) depending on the ascertained characteristic of the measured variable.

Subsequently (3040), it is checked whether a convergence criterion of the cost function has been reached. If this is the case (3050), the currently ascertained parameter $\xi_{opt}$ is adopted as the optimal parameter $\xi_{opt}$.

If this is not the case (3060), the parameter $\xi_{opt}$ is varied. For example, a gradient descent method can be used. Subsequently, with a changed characteristic of the parameter $\xi_{opt}$, the process branches back to step 3020.

Of course, all methods cannot only be implemented in software, but also in hardware, or in a mixed form of hardware and software.

The invention claimed is:

1. Method for ascertaining a time characteristic of a measured variable adjustable by an actuator, wherein a time characteristic of a control variable is applied to the actuator,
wherein the ascertaining is effected by means of a Gaussian process state model of the behavior of the actuator, wherein the time characteristic of the measured variable of the actuator is ascertained on the basis of a parameterizable family of functions, wherein in the parameterizable family of functions a time dependency of a later latent state, is ascertained using a transfer function of the actuator on an earlier latent state of the actuator and an earlier control variable of the actuator is the same as the applicable dependency of the Gaussian process state model,
wherein the parameterizable family of functions is set up, by varying the parameters that parameterize the family of functions, to approximate an a-posteriori probability distribution of at least time characteristics of at least the latent state of the actuator and the transfer function as well as possible, given a time characteristic of the measured variable for an ascertained training data record,
wherein the Gaussian process state model is a sparse Gaussian process state model with inducing Gaussian process targets at pre-determinable pseudo input points,
wherein the dependency of the parameterizable family of functions on Gaussian process targets is given by a second factor, wherein this second factor is a second parameterizable variation function, which has the respective Gaussian process target as an argument, and
wherein the second parameterizable variation function is given by a normal distribution function.

2. Method according to claim 1, wherein the dependency of the parameterizable family of functions on an initial latent state of the actuator is given by a factor, which depends on this initial latent state, this factor being given by a parameterizable variation function, in particular by a normal distribution.

3. Method according to claim 1, wherein a predicted time trend of the latent state of the actuator is ascertained by recursively ascertaining a sample of the predicted time trend of the latent state at a later point in time from the parameterizable variation function of the predicted latent state at the later point in time given the predicted latent state at an earlier point in time, the time characteristic of the measured variable of the actuator being chosen on the basis of the predicted time trend of the latent state.

4. Method according to claim 3, wherein an initial latent state of the predicted time trend of the latent state is predetermined randomly.

5. Method according to claim 3, wherein an initial latent state from the parameterizable variation function is ascertained by a distribution function of the initial state given the ascertained training data record, the characterizing parameters of which can be trained by back propagation.

6. Method according to claim 1, wherein an optimal control variable is ascertained on the basis of a characteristic of the measured variable ascertained by means of the method according to claim 1.

7. Method according to claim 6, wherein the actuator is controlled by means of the optimal control variable.

8. Actuator control system which is set up to control an actuator by means of the method according to claim 7.

9. Method for training the actuator control system according to claim 8, wherein parameters of the parameterizable families of functions and/or deterministic parameters are adapted such that they approximate an a-posteriori probability distribution of at least time characteristics of at least the latent state of the actuator and the transfer function as well as possible, given a time characteristic of the measured variable for an ascertained training data record.

10. Method for ascertaining at least one optimal parameter which characterizes a control strategy of an actuator control system, which is set up to control an actuator with a control variable on the basis of this control strategy,
wherein, when using the control strategy, the time characteristic of a measurement variable that is adjustable by the actuator is ascertained by means of the method according to claim 1, and on the basis of the characteristic of the measured variable thus ascertained, the at least one optimal parameter is ascertained.

11. Prediction system set up to carry out the method according to claim 1.

* * * * *